US011357794B2

(12) United States Patent
Almås

(10) Patent No.: US 11,357,794 B2
(45) Date of Patent: Jun. 14, 2022

(54) PREPARATIONS FOR CONTROLLED-RELEASE OF HYPOCHLOROUS ACID

(71) Applicant: WIAB WATER INNOVATION AB, Malmo (SE)

(72) Inventor: Geir Hermod Almås, Oslo (NO)

(73) Assignee: WIAB WAFER INNOVATION AB, Malmo (SE)

( * ) Notice: Subject to any disclaimer, the term of this patent is extended or adjusted under 35 U.S.C. 154(b) by 273 days.

(21) Appl. No.: 15/852,767

(22) Filed: Dec. 22, 2017

(65) Prior Publication Data

US 2018/0117081 A1 May 3, 2018

Related U.S. Application Data

(63) Continuation-in-part of application No. 15/612,571, filed on Jun. 2, 2017, which is a continuation-in-part of application No. 15/267,220, filed on Sep. 16, 2016, which is a continuation of application No. 15/167,076, filed on May 27, 2016, now Pat. No. 10,675,299, which is a continuation-in-part of application No. 14/618,820, filed on Feb. 10, 2015, and a continuation-in-part of application No. 14/618,799, filed on Feb. 10, 2015, now Pat. No. 10,577,244, said application No. 14/618,820 is a continuation-in-part of application No. 13/770,738, filed on Feb. 19, 2013, now Pat. No. 9,492,479, said application No. 14/618,799 is a continuation of application No. 13/770,738, filed on Feb. 19, 2013, now Pat. No. 9,492,479.

(60) Provisional application No. 62/438,198, filed on Dec. 22, 2016, provisional application No. 62/438,204, filed on Dec. 22, 2016, provisional application No. 62/438,189, filed on Dec. 22, 2016, provisional application No. 62/438,202, filed on Dec. 22, 2016, provisional application No. 61/600,344, filed on Feb. 17, 2012.

(51) Int. Cl.
| | |
|---|---|
| *A61K 33/20* | (2006.01) |
| *A61K 33/30* | (2006.01) |
| *A61K 31/19* | (2006.01) |
| *A61K 9/51* | (2006.01) |
| *A61K 9/00* | (2006.01) |
| *C01B 11/04* | (2006.01) |

(52) U.S. Cl.
CPC ............ *A61K 33/20* (2013.01); *A61K 9/0014* (2013.01); *A61K 31/19* (2013.01); *C01B 11/04* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2,438,781 A | 3/1948 | Kamlet | |
| 4,017,592 A | 4/1977 | Penard et al. | |
| 4,983,634 A | 1/1991 | Corby | |
| 5,152,915 A | 10/1992 | Ralston, Jr. et al. | |
| 5,456,211 A | 10/1995 | Stevenson | |
| 6,333,054 B1 | 12/2001 | Rogozinski | |
| 6,564,508 B1 | 5/2003 | Buchan | |
| 6,627,207 B1 | 9/2003 | Petersen | |
| 6,764,693 B1* | 7/2004 | Smith | A61K 33/30 424/450 |
| 8,449,916 B1 | 5/2013 | Bellaire et al. | |
| 8,784,900 B2 | 7/2014 | Northey | |
| 2006/0141017 A1* | 6/2006 | Kling | A61K 47/44 424/445 |
| 2008/0008621 A1 | 1/2008 | Ikeda et al. | |
| 2009/0247485 A1 | 10/2009 | Ahmed et al. | |
| 2009/0258083 A1 | 10/2009 | Calderon | |
| 2012/0148516 A1 | 6/2012 | Abel et al. | |
| 2015/0150906 A1 | 6/2015 | Hinderson et al. | |
| 2015/0150907 A1* | 6/2015 | Hinderson | A61K 33/20 424/666 |
| 2015/0264935 A1* | 9/2015 | Chang | A01N 59/00 424/600 |
| 2016/0271171 A1 | 9/2016 | Almas | |
| 2017/0266227 A1 | 9/2017 | Almas | |

FOREIGN PATENT DOCUMENTS

| | | |
|---|---|---|
| EP | 1829449 A1 | 9/2007 |
| JP | H10309582 A | 11/1998 |
| JP | 2003040716 A | 2/2003 |
| JP | 2007-326050 A | 12/2007 |
| JP | 2011056377 A | 3/2011 |
| JP | 2011-229833 A | 11/2011 |

(Continued)

OTHER PUBLICATIONS

Akbarzadeh, A., Rezaei-Sadabady, R., Davaran, S. et al. "Liposome: classification, preparation, and applications." Nanoscale Res Lett (2013) 8: 102. https://doi.org/10.1186/1556-276X-8-102.*

Mozafari M.R. (2010) Nanoliposomes: Preparation and Analysis. In: Weissig V. (eds) Liposomes. Methods in Molecular Biology (Methods and Protocols), vol. 605. Humana Press.*

Borkow, Gadi, and Jeffrey Gabbay. "Copper, an ancient remedy returning to fight microbial, fungal and viral infections." Current Chemical Biology 3.3 (2009): 272-278.*

(Continued)

*Primary Examiner* — Bethany P Barham
*Assistant Examiner* — Peter Anthopolos
(74) *Attorney, Agent, or Firm* — Brown Rudnick LLP; Thomas C. Meyers

(57) ABSTRACT

Provided are anti-microbial compositions that include an aqueous solution of hypochlorous acid encapsulated in a nanoparticle that allows for controlled release of hypochlorous acid. Also provided are methods of making and using such compositions.

8 Claims, 16 Drawing Sheets

(56) References Cited

FOREIGN PATENT DOCUMENTS

| WO | 1994021125 | A1 | 9/1994 |
|---|---|---|---|
| WO | 2001028336 | A1 | 4/2001 |
| WO | 2005065383 | A2 | 7/2005 |
| WO | 2013121294 | A1 | 8/2013 |
| WO | 2017203364 | A1 | 11/2017 |

OTHER PUBLICATIONS

Grijalvo, Santiago, et al. "Biodegradable liposome-encapsulated hydrogels for biomedical applications: A marriage of convenience." Biomaterials science 4.4 (2016): 555-574.*

Park, Sung-Hee, et al. "Effects of silver nanoparticles on the fluidity of bilayer in phospholipid liposome." Colloids and Surfaces B: Biointerfaces 44.2-3 (2005): 117-122.*

International Search Report and Written Opinion dated Jul. 30, 2013, for International Application No. PCT/IB2013/000682, filed Feb. 19, 2013 (7 pages).

Kuroiwa, K., et al., "Augmenting effect of acetic acid for acidification on bactericidal activity of hypochlorite solution", Lett. Applied Microbiol., 2003, pp. 46-49 (4 Pages).

Wang, L., et al., "Hypoohlorous Acid as a Potential Wound Care Agent", J Burns Wounds, 2007, pp. 65-79 (15 Pages).

Dash, Sukalyan et al. "Oxidation by Permanganate: Synthetic and Mechanistic Aspects," Tetrahedron, vol. 65, 2009, pp. 707-739 (33 Pages).

Boddie, R.L. et al., "Efficacy of Teat Dips Containing a Hypochlorous Acid Germicide Against Experimental Challenge with *Staphylococcus aureus* and *Streptococcus agalactiae*", J. Dairy Sci., 1996, pp. 1683-1688 (6 Pages).

Schmittinger, P. et al. "Chlorine", Wiley, 2000, pp. 160-164 (7 Pages).

Plaizier-Vercammen, Jacqueline, "Rheological Properties of Laponite XLG, A Synthetic Purified Hectorite", Die Pharmazie: An International Journal of Pharmaceutical Sciences, Govi Verlag Pharmazeutischer Verlag GMBH, DE, vol. 47, No. 11, Nov. 1992, pp. 856-861 (6 Pages).

International Search Report and Written Opinion of the International Searching Authority dated Sep. 8, 2017 for International Application No. PCT/IB2017/000757 (17 Pages).

Puttaiah, R., et al., "Dental Unit Water Line Treatment with Sodium Hypochlorite and Acetic Acid", Michochemical Journal, 1998, pp. 333-340 (8 Pages).

International Search Report and Written Opinion of the International Searching Authority dated May 17, 2018 for International Application No. PCT/IB2017/001728 (17 Pages).

Dasgupta et al., Mol. Pharmaceutics 12:3479-3489.

Feng et al. 2007, J. Environ. Eng. Sci. 6, 277-284.

Gao, et al. The Journal of Antibiotics, (2011) 64, 625-634.

Grijalvo, et al., The Royal Socitey of Chemistry, Biomater. Sci., 2016, 4, 555-574.

Lee et al., Dovepress, International Journal of Nanomedicine, 2016:11 285-297.

Tzanavaras et al., 2007 Central European Journal of Chemistry, pp. 1-12.

Weiniger et al., 2012 Anaesthesia, 67, 906-916.

Binnebose, et al., 2015 Journal PLOS Neglected Tropical Disease, DOI:10. 1371, pp. 1-18.

Campos, et al., Scientific Reports, pp. 1-14.

* cited by examiner

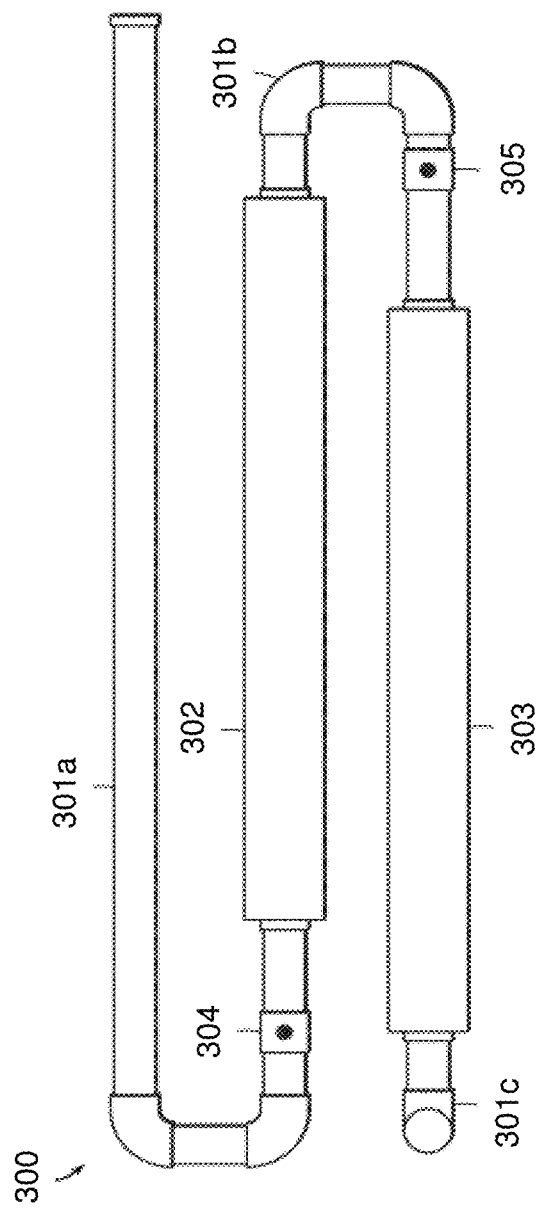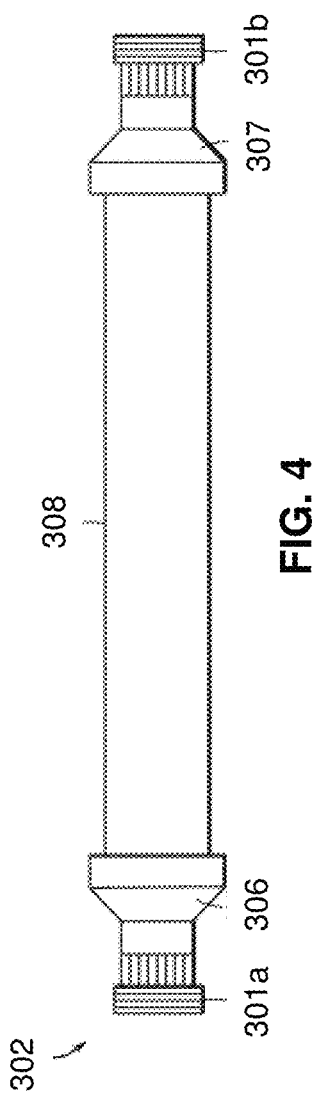

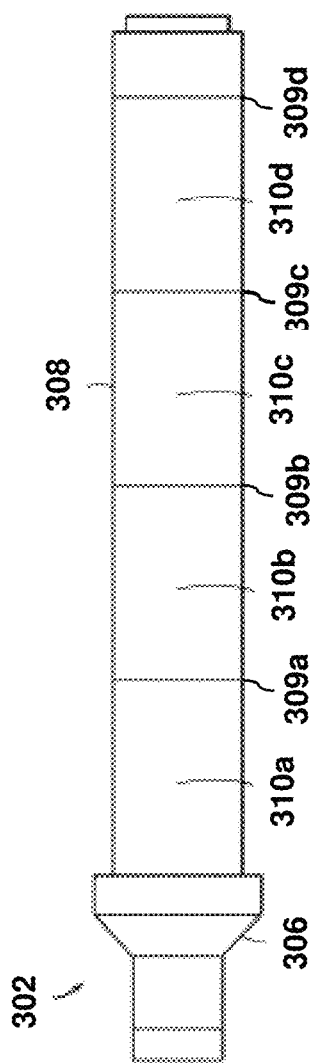
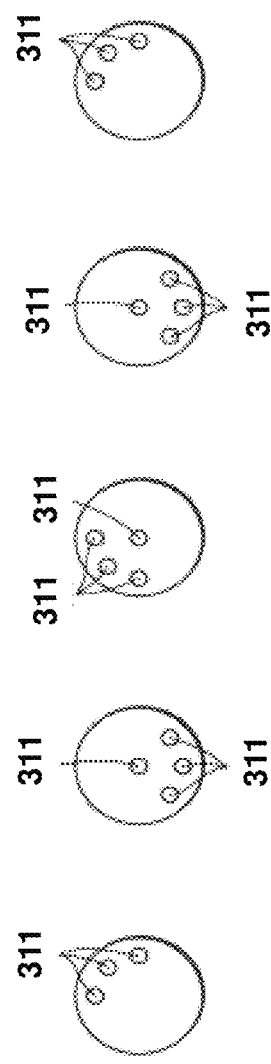
FIG. 5
FIG. 6

24 hours filter-grown P. aeruginosa biofilms log10 reduction cfu/ml

After 2 h treatment

| HAc / HOCl | 0 ppm | 50 ppm | 100 ppm | 150 ppm | 200ppm |
|---|---|---|---|---|---|
| 0.25% | | | 0.60 | 5.57 | 8.75 |
| 0.5% | | | 0.97 | 5.34 | 8.75 |
| 1% | 0.18 | 0.35 | 1.11 | 3.77 | 4.00/8.75 |
| 1.5% | 0.00 | 0.00 | 1.43 | | 8.75 |
| 2% | 0.19 | 0.00 | 1.42 | | 8.75 |

After 2+2 h treatment

| HAc / HOCl | 0 ppm | 50 ppm | 100 ppm | 150 ppm | 200ppm |
|---|---|---|---|---|---|
| 0.25% | | | 3.00 | 8.66 | 8.75 |
| 0.5% | | | 7.31 | 8.66 | 8.75 |
| 1% | 0.15 | 1.86 | 8.85 | 8.80 | 8.80 |
| 1.5% | 0.00 | 1.08 | 8.85 | | 8.75 |
| 2% | 0.00 | 1.23 | 8.85 | | 8.75 |

FIG. 19

PREPARATIONS FOR CONTROLLED-RELEASE OF HYPOCHLOROUS ACID

RELATED APPLICATIONS

This application claims priority to and the benefit of U.S. Provisional Patent Application Ser. No. 62/438,189, filed Dec. 22, 2016, U.S. Provisional Patent Application Ser. No. 62/438,198, filed Dec. 22, 2016, U.S. Provisional Patent Application Ser. No. 62/438,202, filed Dec. 22, 2016, and U.S. Provisional Patent Application Ser. No. 62/438,204, filed Dec. 22, 2016; and this application is a continuation-in-part of U.S. patent application Ser. No. 15/612,571, filed Jun. 2, 2017.

Additionally, U.S. patent application Ser. No. 15/612,571 claims priority to and the benefit of U.S. Provisional Patent Application Ser. No. 62/438,198, filed Dec. 22, 2016, and U.S. Provisional Patent Application Ser. No. 62/438,204, filed Dec. 22, 2016; and is a continuation-in-part of U.S. patent application Ser. No. 15/267,220, filed Sep. 16, 2016, which is a continuation of U.S. patent application Ser. No. 15/167,076, filed May 27, 2016, which is: (1) a continuation-in-part of U.S. patent application Ser. No. 14/618,820, filed Feb. 10, 2015, which is a continuation-in-part of U.S. patent application Ser. No. 13/770,738, filed Feb. 19, 2013, which claims priority to and the benefit of U.S. Provisional application Ser. No. 61/600,344, filed Feb. 17, 2012; and (2) a continuation-in-part of U.S. patent application Ser. No. 14/618,799, filed Feb. 10, 2015, which is a continuation of U.S. patent application Ser. No. 13/770,738, filed Feb. 19, 2013, which claims priority to and the benefit of U.S. Provisional application Ser. No. 61/600,344, filed Feb. 17, 2012.

The contents of each of the above-referenced applications are incorporated by reference herein in their entirety.

TECHNICAL FIELD

The invention generally relates to compositions of hypochlorous acid and methods of manufacture and use thereof.

BACKGROUND

Bacterial and viral infections can pose serious medical problems. Microbial infections commonly result from contact with objects contaminated with bacteria or viruses. In medical environments, people are particularly vulnerable to infection from contaminated surgical devices, such as surgical instruments, tubing, fasteners, and bandages. Outside of the operating room, bandages and devices used to treat open wounds are common sources of bacterial and viral infections. Implements used in food processing and preparation, such as utensils, bowls, dishes, cutting boards, and storage devices, also carry a high risk of transmitting microbial infections. Microbial infections are also frequently transmitted via contact with fixtures in public restrooms, schools, childcare centers, stores, restaurants, gymnasiums, and other public venues.

Although methods and compositions exist to minimize microbial contamination of objects that have a high risk of transmitting infections, each has its limitations. For example, oxidizing agents, like sodium hypochlorite (NaOCl), the active ingredient in bleach, are effective at killing microbes but are harmful to human cells. Consequently, surfaces treated with bleach or similar reagents must be thoroughly rinsed before they can safely contact food or human tissue. The same is true for harsh detergents, such as those that are used in automatic dishwashers. Alternatively, autoclaves kill microbes through the use of high temperature and pressure rather than potentially toxic chemicals. Because autoclaving leaves an object with no chemical residue that could harm humans, autoclaving is often used to sterilize surgical instruments. However, autoclaving leaves an object with no persistent protection against microbial contamination. Consequently, to prevent transmission of microbial infection, autoclaved objects must be preserved in a sterile environment until they are used. Thus, there currently exists no method or composition that provides an object with persistent antimicrobial protection but is not also deleterious to humans.

SUMMARY

The invention provides compositions having an aqueous solution of hypochlorous acid (HOCl) in a nanoparticle that allows for controlled release of hypochlorous acid to provide persistent anti-microbial protection. Hypochlorous acid is a weak acid that rapidly inactivates microorganisms such as bacteria, algae, and fungi. Humans, however, can tolerate hypochlorous acid because they produce taurine, an organic compound that neutralizes hypochlorous acid. Consequently, compositions of the invention have anti-microbial activity but are generally not harmful to humans. Compositions of the invention release hypochlorous acid gradually over time. Therefore, surfaces coated with such compositions maintain their anti-microbial properties long after initial application of the composition to the surface. Because compositions of the invention provide prolonged anti-microbial activity and are non-toxic to humans, they are useful for treating objects to prevent transmission of bacterial infections in a wide swath of environments. For example, claimed compositions have applications in the medical, foodservice, food retail, agricultural, wound care, laboratory, hospitality, dental, or floral settings.

In certain aspects, the invention provides an anti-microbial composition that includes an aqueous solution of hypochlorous acid encapsulated in a nanoparticle. The composition or the aqueous solution may be substantially free of air. The composition or the aqueous solution may also be substantially free of chlorine gas. The aqueous solution may have a pH from about 4.5 to about 7.5. The aqueous solution may include a buffering agent. The buffering agent may be acetic acid or other organic acids.

The nanoparticle housing hypochlorous acid and other reactants may comprise a polymer. For example, a nanoparticle may include acrylic acid, carrageenan, cellulosic polymers, ethyl cellulose, hydroxypropyl cellulose, chitosan, cyclodextrins, gelatin, guar gum, high amylase starch, locust bean gum, pectin, poly(D,L-lactide-co-glycolide acid), poly(lactic acid), poly(xylitol adipate salicylate), and polyanhydride, poly(ethylene oxide), poly(ethyleneimine), polyglycerol ester of a fatty acid, polyvinyl alcohol, povidone, sodium alginate, or xanthan gum. The nanoparticle may be a liposome or a hydrogel.

Compositions of the invention may include an anti-metabolic agent. The anti-metabolic agent may be a metal ion. For example, the anti-metabolic agent may be zinc, copper, or silver.

In another aspect, the invention provides methods of making an anti-microbial composition that includes an aqueous solution of hypochlorous acid encapsulated in a nanoparticle. Preferred methods include mixing together in water in a chamber from which air has been purged a compound that generates a proton ($H^+$) in water and a compound that generates a hypochlorite anion ($OCl^-$) in water, thereby to produce an air-free aqueous solution of hypochlorous acid; and encapsulating the air-free aqueous solution of hypochlorous acid in a nanoparticle.

The compound that generates the proton and the compound that generates the hypochlorite anion may be added sequentially. The compound that generates the proton may be introduced to the water first, and the compound that generates the hypochlorite anion may be introduced to the water second. Alternatively, the compound that generates the hypochlorite anion may be introduced to the water first, and the compound that generates the proton may be introduced to the water second. The mixing may involve sequential addition of the compounds, the sequence may be repeated in an iterative manner.

The solutions of the compound that generates the proton and of the compound that generates the hypochlorite anion may be added in limited quantities. For example, no more than 0.6 ml of a solution of the compound that generates the proton may be added at one time, or no more than 0.6 ml of a solution of the compound that generates the hypochlorite anion may be added at one time.

The water may be tap water or purified water. A buffering agent may be added to the water. The buffering agent may be an acetic acid (or other organic acids) buffer or a phosphate buffer. The water may have a buffering capacity from about pH 3.5 to about pH 9.0. The pH of the water may be increased prior to addition of the compound that generates the proton.

The compound that generates the hypochlorite anion may be sodium hypochlorite (NaOCl), $Mg(OCl)_2$, or $Ca(OCl)_2$. The compound that generates the proton may be acetic acid (or other organic acids), sulfuric acid, or HCl.

Compounds for use in the invention may be mixed turbulently. Turbulent mixing may be used when the proton-generating compound is added to water, or turbulent mixing may be used subsequent to the addition of the proton-generating compound. Turbulent mixing may be used when the hypochlorite-generating compound is added to water, or turbulent mixing may be used subsequent to the addition of the hypochlorite-generating compound. When the compounds are added sequentially, turbulent mixing may be used during or subsequent to addition of the first compound, during or subsequent to addition of the second compound, or during or subsequent to addition of both the first and second compounds.

Disclosed methods may be performed without the use of chlorine gas or electrolysis. The methods may entail applying pressure to flow water through a pipe.

In some embodiments, the methods of making an anti-microbial composition entail producing an aqueous solution of hypochlorous acid that includes performing a series of steps in an air-free environment and under pressure. The steps include: introducing hydrochloric acid to a flow of water; turbulently mixing the HCl with the flowing water in mixing device from which air has been purged; introducing sodium hypochlorite to the water after the water has exited the mixing device; and turbulently mixing the sodium hypochlorite with the flowing water in another mixing device from which air has been purged.

In another aspect, the invention provides a method of disinfecting a surface of a device. The method includes the step of applying to the surface of a device an anti-microbial composition that includes an aqueous solution of hypochlorous acid encapsulated in a nanoparticle.

The device may be a medical or dental device. For example, the device may be a device used in surgery, dentistry, orthodontics, wound treatment. For example, the device may be a prosthesis, catheter, trocar, artificial organ, artificial tissue, plate, mesh, drill, pacemaker, defibrillator, pump, implantable device, scalpel, knife, forceps, vacuum, stapler, suture, staple, wire, rod, nail, fastener, screw, pin, tubing, sponge, tape, bandage, light, mirror, stent, valve, shunt, contraceptive device, denture, crown, compression sleeve, glove, mask, cap, gown, or shoe covering.

The device may be a device used in food processing, preparation, or storage. For example, the device may be knife, fork, spoon, utensil, cutting board, blade, plate, dish, bowl, wrapper, container, lid, bottle, or jar.

BRIEF DESCRIPTION OF THE DRAWINGS

FIG. 3 is a schematic showing an exemplary system for producing hypochlorous acid according to methods of the invention.

FIG. 4 is a schematic showing a magnified view of the mixing device shown in FIG. 3.

FIG. 5 is a schematic showing an internal view of the mixing chamber of the mixing device.

FIG. 6 is a schematic showing a front view of the members that divide the mixing chamber into a plurality of sub-chambers. This view shows the apertures in the members.

FIGS. 15-21 provide data on the reduction of various biofilms when exposed to compositions of acetic acid and hypochlorous acid at different concentrations, compared with commercially available biofilm treatments.

DETAILED DESCRIPTION

The invention generally relates to compositions and methods in which a stable aqueous solution of hypochlorous acid is encapsulated in nanoparticles that allow controlled release of the acid from the nanoparticles. The basis of compositions and methods of the invention is the protonation of the hypochlorite ion ($OCl^-$). Using HCl or acetic acid (HAc)

and NaOCl as an example, the protonation is accomplished by introducing an acid (e.g., HCl) to the solution, which results in the following reaction:

or

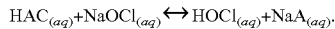

The hypochlorous acid in aqueous solution partially dissociates into the anion hypochlorite (OCl$^-$). Thus, in aqueous solution there is always an equilibrium between the hypochlorous acid and the anion (OCl$^-$). This equilibrium is pH-dependent, and at higher pH the anion dominates. In aqueous solution, hypochlorous acid is also in equilibrium with other chlorine species, such as chlorine gas, $Cl_2$, and various chlorine oxides. At acidic pH, chlorine gases become increasingly dominant, while at neutral pH the different equilibria result in a solution dominated by hypochlorous acid. Thus, it is important to control exposure to air and pH in the production of hypochlorous acid.

Additionally, the concentration of protons (H$^+$) affects the stability of the product. The invention recognizes that the proton concentration can be controlled by using an acid that has a lesser ability at a given pH to donate a proton (i.e., the acid can provide buffering capacity). For example, conducting the process with acetic acid (or other organic acids) instead of hydrochloric acid is optimal when the desired pH of the final solution is approximately the pKa of acetic acid. This can be achieved by mixing ratios in water of 250× or greater, meaning 1 part proton donor at 100% concentration (e.g., HCl or acetic acid) to 250 parts water.

Figure 1:
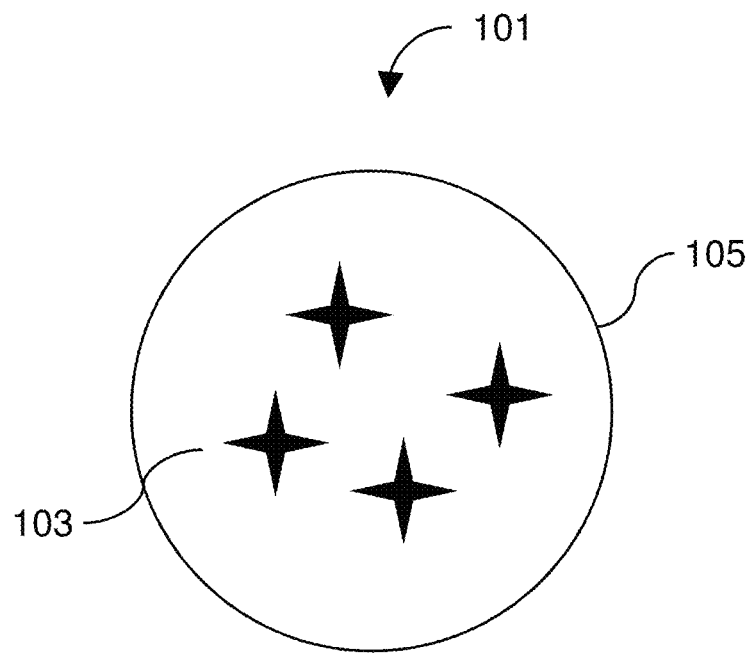
FIG. 1 shows an anti-microbial composition that includes an aqueous solution of hypochlorous acid encapsulated in a nanoparticle.

FIG. 1 shows an anti-microbial composition 101 comprising an aqueous solution 103 of hypochlorous acid encapsulated in a nanoparticle 105. The aqueous solution 103 of hypochlorous acid is made by a method described herein to produce a solution in which the acid is stable. The stable hypochlorous acid solution 103 is then encapsulated in nanoparticle 105. The nanoparticle allows gradual release of the hypochlorous acid.

The nanoparticle may be any type of nanoparticle that provides controlled release of hypochlorous acid from the nanoparticle. The nanoparticle may comprise a polymer, such as an organic polymer. Examples of polymers suitable for controlled-release nanoparticles include acrylic acid, carrageenan, cellulosic polymers (e.g., ethyl cellulose or hydroxypropyl cellulose), chitosan, cyclodextrins, gelatin, guar gum, high amylase starch, hyaluronic acid, locust bean gum, pectin, polyacrylamide, poly(D,L-lactide-co-glycolide acid), poly(lactic acid), poly(xylitol adipate salicylate), polyanhydride, poly(ethylene oxide), poly(ethyleneimine), polyglycerol ester of a fatty acid, polysaccharides, polyvinyl alcohol, povidone, sodium alginate, and xanthan gum. For details on the use of polymers to form controlled-release nanoparticles, see Binnebose, et al., *PLOS Negl Trop Dis* 9:e0004713 (2015); Campos, et al., *Scientific Reports* 5:13809 (2015); Dasgupta et al., *Mol. Pharmaceutics* 12:3479-3489; Gao, et al., *The Journal of Antibiotics* 64:625-634, (2011); Lee, et al., *International Journal of Nanomedicine* 11:285-297 (2016); and U.S. Pat. No. 8,449,916 (incorporated by reference). The nanoparticle may contain an aluminosilicate (such as a zeolite, e.g., analcime, chabazite, clinoptilolite, heulandite, leucite, montmorillonite, natrolite, phillipsite, or stilbite), calcium ammonium nitrate, hydroxyapatite (e.g., urea-modified hydroxyapatite), metal hydroxide, metal oxide, polyphosphate, or silicon compound (e.g., silicon dioxide). The nanoparticle may contain lipids, i.e., it may be a lipid nanoparticle. The nanoparticle may include a liposome. For details on the use of liposomes to form controlled-release nanoparticles, see Weiniger et al., *Anaesthesia* 67:906-916 (2012). The liposome may be multi-lamellar. The nanoparticle may contain a gel, sol-gel, emulsion, colloid, or hydrogel. For details on the use of hydrogels to form controlled-release nanoparticles, see Grijalvo et al., *Biomater. Sci.* 4:555 (2016). The nanoparticle may contain a combination of formats, such as a hydrogel encapsulated within a liposome. The nanoparticle may have a core-shell structure. The nanoparticle may be biodegradable.

A nanoparticle that allows controlled release of hypochlorous acid permits diffusion of the acid to occur more slowly than the acid would diffuse from an equal volume of the same aqueous solution of hypochlorous acid that is not encapsulated in a nanoparticle. The controlled release of hypochlorous acid may be due to permeability characteristics of the nanoparticle, e.g., a nanoparticle that is partially or poorly permeable to hypochlorous acid. A controlled-release nanoparticle may be a nanoparticle that releases hypochlorous acid due to degradation of the nanoparticle or impairment of its structural integrity in a time-dependent manner. Release of hypochlorous acid from the nanoparticle may be triggered by environmental conditions, such as pH, temperature, light, pressure, redox conditions, or the presence of a particular chemical.

Figure 2:
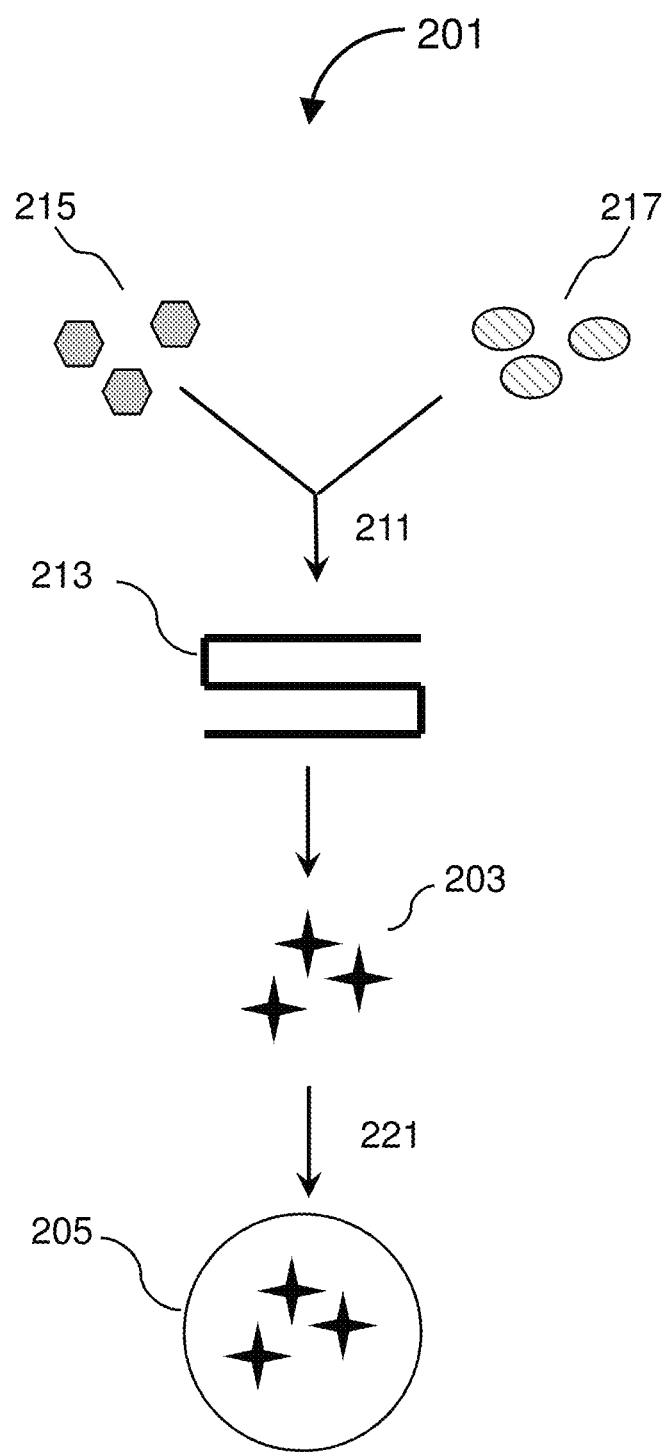
FIG. 2 is an illustration of a method of making an anti-microbial composition that includes an aqueous solution of hypochlorous acid encapsulated in a nanoparticle.

FIG. 2 is an illustration of a method 201 of making an anti-microbial composition that includes an aqueous solution 203 of hypochlorous acid encapsulated in a nanoparticle 205. The method entails mixing 211 in water in a chamber 213 from which air has been purged a compound 215 that generates a proton (H$^+$) in water and a compound 217 that generates a hypochlorite anion (OCl$^-$) in water. The mixing 211 produces an air-free aqueous solution 203 of hypochlorous acid. The solution 203 is then encapsulated 221 in a nanoparticle 205. The encapsulation may be performed in an air-free environment to produce a composition that is substantially free of air.

In certain embodiments, methods of the invention involve mixing, in water in an air-free environment, a compound that generates a proton (H$^+$) in water and a compound that generates a hypochlorite anion (OCl$^-$) in water to produce an air-free aqueous solution of hypochlorous acid. The water may be tap water or purified water, such as water purchased from a water purification company, such as Millipore (Billerica, Mass.). Generally, the pH of the water is maintained from about 4.5 to about 9 during the method, but the pH may go above and below this range during the production process. Conducting methods of the invention in an air-free environment prevents the build-up of chlorine gases during the production process. Further, conducting methods of the invention in an air-free environment stabilized the produced HOCl.

Any compound that produces a hypochlorite anion (OCl$^-$) in water may be used with methods of the invention. Exemplary compounds include NaOCl and Ca(OCl)$_2$. In particular embodiments, the compound is NaOCl. Any compound that produces a proton (H$^+$) in water may be used with methods of the invention. Exemplary compounds are acids, such as acetic acid, HCl and H$_2$SO$_4$. In particular embodiments, the compound is HCl. In preferred embodiments, the compound is acetic acid because it is a weaker acid with a preferred pKa to HCl, i.e., it donates protons less readily during the reaction than HCl and is better able to maintain the preferred pH.

FIG. 3 shows a fluidic system used to perform methods of the invention. The illustrated system is shown as example only, and it is understood that methods of the invention can be conducted in any suitable vessel, chamber or fluidic system. The system 300 includes a series of interconnected pipes 301a-c with a plurality of mixing devices 302 and 303 in-line with the plurality of pipes 301a-c. The pipes and the mixing devices can be interconnected using seals such that all air can be purged from the system, allowing for methods of the invention to be performed in an air-free environment. In certain embodiments, methods of the invention are also conducted under pressure. Conducting methods of the invention in an air-free environment and under pressure allows for the production of HOCl that does not interact with gases in the air (e.g., oxygen) that may destabilize the produced HOCl.

Pipes 301a-c generally have an inner diameter that ranges from about 5 mm to about 50 mm, more preferably from about 17 mm to about 21 mm. In specific embodiments, the pipes 301a-c have an inner diameter of about 21 mm. Pipes 301a-c generally have a length from about 10 cm to about 400 cm, more preferably from about 15 cm to about 350 cm. In certain embodiments, pipes 101a-c have the same length. In other embodiments, pipes 301a-c have different lengths. In specific embodiments, pipe 301a has a length of about 105 cm, pipe 301b has a length of about 40 cm, and pipe 301c has a length of about 200 cm.

The pipes and mixers can be made from any inert material such that material from the pipes and mixers does not become involved with the reaction occurring within the fluidic system. Exemplary materials include PVC-U. Pipes are commercially available from Georg Ficher AB. The pipes and mixers can be configured to have a linear arrangement such that the pipes and the mixers are arranged in a straight line. Alternatively, the pipes and mixers can have a non-linear arrangement, such that the water must flow through bends and curves throughout the process. System 300 shows a non-linear configuration of the pipes 301a-c and mixers 302 and 303.

Pipe 301a is an inlet pipe that receives the water that will flow through the system. Generally, the water in pipes 301a-c is under a pressure of at least about 0.1 bar, for example, 0.2 bar or greater, 0.3 bar or greater, 0.4 bar or greater, 0.5 bar or greater, 0.7 bar or greater, 0.9 bar or greater, 1.0 bar or greater, 1.2 bar or greater, 1.3 bar or greater, or 1.5 bar or greater. At such pressures, a turbulent water flow is produced, and thus the reagents are introduced to a highly turbulent water flow, which facilitates an initial mixing of the reagents with the water prior to further mixing in the mixing devices 302 and 303.

In order to control the pH during the production process, the incoming water should have a buffering capacity in the range of pH 3.5-9.0, more preferably between 6.0 and 8.0, to facilitate addition of the compound that generates the proton and the compound that generates the hypochlorite anion. The dissolved salts and other molecules found in most tap waters gives the tap water a buffering capacity in the range of pH 5.5-9.0, and thus tap water is a suitable water to be used with methods of the invention.

In certain embodiments, deionized water is combined with known buffering agents to produce water having a buffering capacity in the range of pH 3.5-9.0. One example of a buffer in this particular range is phosphate buffer. For greater process control and consistency, using a formulated deionized water may be preferable to using tap water because tap water can change between locations and also over time. Additionally, using deionized water with known additives also ensures a stable pH of the incoming water flow. This process is discussed in greater detail below.

In particular embodiments, an initial pH of the water prior to addition of either the compound that generates the proton or the compound that generates the hypochlorite anion is at least about 8.0, including 8.1 or greater, 8.2 or greater, 8.3 or greater, 8.4 or greater, 8.5 or greater, 8.6 or greater, 8.7 or greater, 8.8 or greater, 8.9 or greater, 9.0 or greater, 9.5 or greater, 10.0 or greater, 10.5 or greater, or 10.8 or greater. In specific embodiments, the pH of the water prior to addition of either the compound that generates the proton or the compound that generates the hypochlorite anion is 8.4.

Methods of the invention include introducing to the water the compound that generates the proton and the compound that generates the hypochlorite anion in any order (e.g., simultaneously or sequentially) and in any manner (aqueous form, solid form, etc.). For example, the compound that generates the proton and the compound that generates the hypochlorite anion may both be in aqueous solutions that are introduced to the water sequentially, e.g., the compound that generates the proton may be introduced to the water first and the compound that generates the hypochlorite anion may be introduced to the water second. However, methods of the invention include other orders for sequential introduction of the compound that generates the proton and the compound that generates the hypochlorite anion.

System 300 is configured for sequential introduction of reagents to the water flow, and the process is described herein in which the compound that generates the proton is introduced to the water first and the compound that generates the hypochlorite anion is introduced to the water second. In certain embodiments, the compound that generates the proton and the compound that generates the hypochlorite anion are introduced to the water in small aliquots, e.g., from about 0.1 mL to about 0.6 mL. The iterative and minute titrations make it possible to control the pH in spite of additions of acid (compound that generates the proton) and alkali (the compound that generates the hypochlorite anion). In certain embodiments, no more than about 0.6 mL amount of compound that generates the proton is introduced to the water at a single point in time. In other embodiments, no more than about 0.6 mL amount of the compound that generates the hypochlorite anion is introduced to the water at a single point in time.

To introduce the reagents to the water, pipe 301a includes an injection port 304 and pipe 301b includes an injection port 305. The injection ports 304 and 305 allow for the introduction of reagents to the water flow. In this embodiment, the compound that generates the proton is introduced to the water in pipe 301a via injection port 304. The compound that generates the proton is introduced by an infusion pump that is sealably connected to port 304. In this manner, the flow rate, and thus the amount, of compound that generates the proton introduced to the water at any given time is controlled. The infusion pump can be controlled automatically or manually. The rate of introduction of the compound that generates the proton to the water is based upon the incoming water quality (conductivity and pH level) and the pressure and the flow of the incoming water. In certain embodiments, the pump is configured to introduce about 6.5 liters per hour of hydrochloric acid into the water. The acid can be introduced by continuous infusion or in an intermittent manner. Since the water is flowing though the pipes in a turbulent manner, there is an initial mixing of the compound that generates the proton with the water upon introduction of the hydrochloric acid to the water.

FIG. 4 shows a magnified view of the mixing device 302 shown in FIG. 3. Further mixing occurs when the water enters the first mixing device 302. In the illustrated embodiment, the mixing device includes a length of about 5.5 cm and a diameter of about 5 cm. One of skill in the art will recognize that these are exemplary dimensions, and methods of the invention can be conducted with mixing devices having different dimensions from the exemplified dimensions. Mixing device 302 includes a fluidic inlet 306 that sealably couples to pipe 301a and a fluidic outlet 307 that sealably couples to pipe 301b. In this manner, water can enter the mixing chamber 308 of device 302 from pipe 301a and exit the chamber 308 of device 302 through pipe 301b.

FIG. 5 shows an internal view of the chamber 308 of device 302. The mixing device 302 is configured to produce a plurality of fluidic vortexes within the device. The chamber 308 includes a plurality of members 309a-d, the members being spaced apart and fixed within the chamber 308 perpendicular to the inlet and the outlet to form a plurality of sub-chambers 310a-d. Each member 309a-d includes at least one aperture 311 that allows fluid to flow through the member.

FIG. 6 shows a front view of members 309a-d so that apertures 311 can be seen. The size of the apertures will depend on the flow of water and the pressure in the system. Any number of members 309a-d may be fixed in the chamber 308, the number of members 309a-d fixed in the chamber 308 will depend on the amount of mixing desired. In the embodiment shown, four members 309a-d are fixed in the chamber to produce four sub-chambers 310a-d. The members 309a-d may be spaced apart a uniform distance within the chamber 308, producing sub-chambers 310a-d of uniform size. Alternatively, the members 309a-d may be spaced apart at different distances within the chamber 308, producing sub-chambers 310a-d of different sizes. The members 309a-d are of a size such that they may be fixed to an interior wall within the chamber 308. In this manner, water cannot flow around the members and can only pass through the apertures 311 in each member 309a-d to move through mixing device 302. Generally, the members will have a diameter from about 1 cm to about 10 cm. In specific embodiments, the members have a diameter of about 3.5 cm.

A fluidic vortex is produced within each sub-chamber 310a-d. The vortices result from flow of the water through the apertures 311 in each member 309a-d. Methods of the invention allow for any arrangement of the apertures 311 about each member 309. The illustration shows various, non-limiting examples of arrangements of the apertures 311 within a member 309. The apertures 311 shown are circular, but they may be of any shape. In certain embodiments, all of the apertures 311 are located within the same place of the members 309a-d. In other embodiments, the apertures 311 are located within different places of the members 309a-d. Within a single member 309, all of the apertures 311 may have the same diameter. Alternatively, within a single member 309, at least two of the apertures 311 may have different sizes. In other embodiments, all of the apertures 311 within a single member 309 have different sizes.

In certain embodiments, apertures 311 in a member 309 have a first size, and apertures 311 in a different member 309 have a different second size. In other embodiments, apertures 311 in at least two different members 309 have the same size. The size of the apertures will depend on the flow of water and the pressure in the system. Exemplary aperture diameters are from about 1 mm to about 1 cm. In specific embodiments, apertures have a diameter of about 6 mm.

The solution enters mixing device 302 through inlet 306, which is sealably mated with pipe 301a. The solution enters the chamber 308, and turbulent mixing occurs in each of sub-chambers 310a-d as the solution passes through members 309a-d via the apertures 311 in each member 309a-d. After mixing in the final sub-chamber 310d, the water exits the chamber 308 via the fluidic outlet 307, which is sealably mated to pipe 301b.

The compound that generates the hypochlorite anion is next introduced to the solution that is flowing through pipe 301b via injection port 305. The compound that generates the hypochlorite anion is introduced by an infusion pump that is sealably connected to port 305. In this manner, the flow rate, and thus the amount, of compound that generates the hypochlorite anion introduced to the water at any given time is controlled. The infusion pump can be controlled automatically or manually. The rate of introduction of the compound that generates the hypochlorite anion to the water is based upon properties of the solution (conductivity and pH level) and the pressure and flow rate of the solution. In certain embodiments, the pump is configured to introduce about 6.5 liters per hour of compound that generates the hypochlorite anion into the solution. The compound can be introduced by continuous infusion or in an intermittent manner. Since the solution is flowing though the pipes in a turbulent manner, there is an initial mixing of the compound that generates the hypochlorite anion with the solution upon introduction of the compound that generates the hypochlorite anion to the solution.

Further mixing occurs when the solution enters the second mixing device 303. Mixing device 303 includes all of the features discussed above with respect to mixing device 302. Mixing device 303 may be configured the same as, or differently from, mixing device 302. For example, the two mixing devices may have the same or different number of sub-chambers, the same or different diameter of apertures, the same or different sizes of sub-chambers, etc. However, like mixing device 302, mixing device 303 is configured to produce a fluidic vortex within each sub-chamber.

The solution enters mixing device 303 through an inlet in the device, which is sealably mated with pipe 301b. The solution enters the mixing chamber, and turbulent mixing occurs in each sub-chamber of the mixing device as the solution passes through members in the chamber via the apertures in each member. After mixing in the final sub-chamber, the water exits the chamber via the fluidic outlet in the mixing device, which is sealably mated to pipe 301c.

At this point, the reaction has been completed, and the HOCl has been formed. The production is controlled in-line by measuring pH and conductivity. The pH is used in combination with conductivity based on a pre-calibrated relationship between the conductivity and concentration of HOCl measured with spectrophotometry. The measured conductivity is a measure of the solvent's ability to conduct an electric current.

Figure 7:
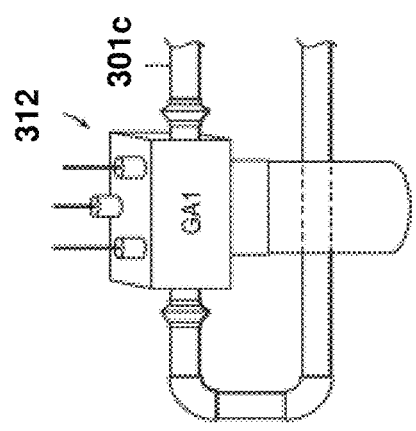
FIG. 7 is a schematic showing a valve configured with measuring sensors for switching from a waste line to a product collection line.

FIG. 7 shows a pipe 301c connected to a switch valve 312. The valve 312 includes the pH meter and the conductivity measuring device. These devices measure the concentration (ppm), purity, and pH of the HOCl being produced and provide feedback for altering such properties of the produced HOCl.

Figure 8:
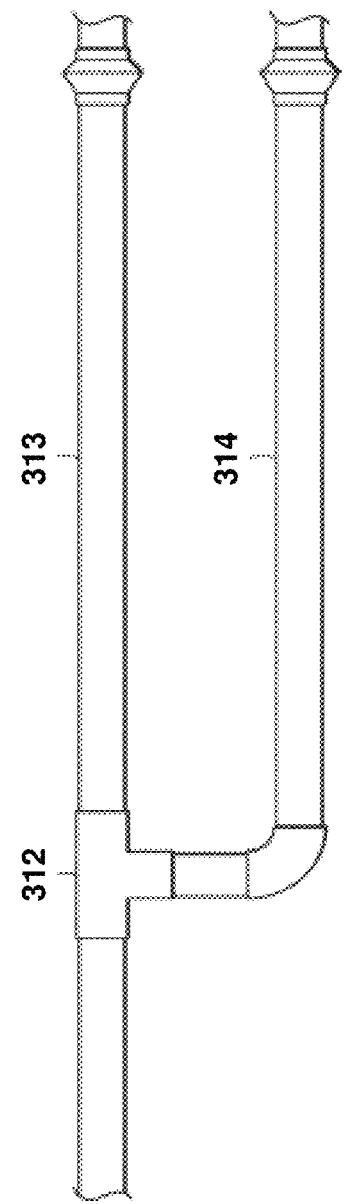
FIG. 8 is a schematic showing a valve in-line with the waste line and the product collection line.

FIG. 8 shows a switch valve 312 that switches between a waste line 313 and a product collection line 314. Once the HOCl being produced in pipe 301c meets the required concentration, purity, and pH, the valve 312 switches from the waste line 313 to the product collection line 314 to collect the desired product.

The HOCl that has been produced in an air-free manner is collected and bottled in an air-free manner. Placing liquids into a bottle in an air-free manner is known in the art. An exemplary method includes placing an inflatable vessel (such as a balloon) into a bottle. The inflatable vessel is connected directly to the collection line 314, and the HOCl is pumped directed into the inflatable vessel in the bottle without ever being exposed to air. Another method involves filling the bottles under vacuum. Another air-free filling method involves filling the bottles in an environment of an inert gas that does not interact with the HOCl, such as an argon environment.

The produced hypochlorous acid is air-free and has a pH from about 4.5 to about 7.5. However, the pH of the produced HOCl can be adjusted post-production by adding either acid (e.g., HCl) or alkali (e.g., NaOCl) to the produced hypochlorous acid. For example, a pH of between about 4.5 and about 7 is particularly suitable for the application of reprocessing heat sensitive medical instruments. However, different pH levels may be preferable for other applications, such as the processing of poultry and fish, general agricultural and petrochemical uses, or the breaking down of bacterial biofilm and water treatment.

The process can be performed manually or in an automated manner. Fluidic systems described herein can be operably connected to a computer that controls the production process. The computer may be a PCL-logic controller system. The computer opens and closes the valves for the water inlet, the waste water outlet, and the product outlet according to the feedback received from the sensors in the system (e.g., conductivity, pH, and concentration of product (ppm) being produced). The computer can also store the values for the water pressures and water amounts and can adjust these according to the feedback received from the sensors regarding the properties of the HOCl being produced. The computer can also control the infusion pumps that inject the reagents into the water for the production process.

The process can be performed iteratively in that pipe 301c can be attached to a second fluidic system, and the produced HOCl is then flowed through the second system where the process described above is repeated using HOCl instead of water as the starting solution. In this manner, an increased yield of HOCl is produced. Any number of fluidic systems may be interconnected with methods of the invention.

Figure 9:
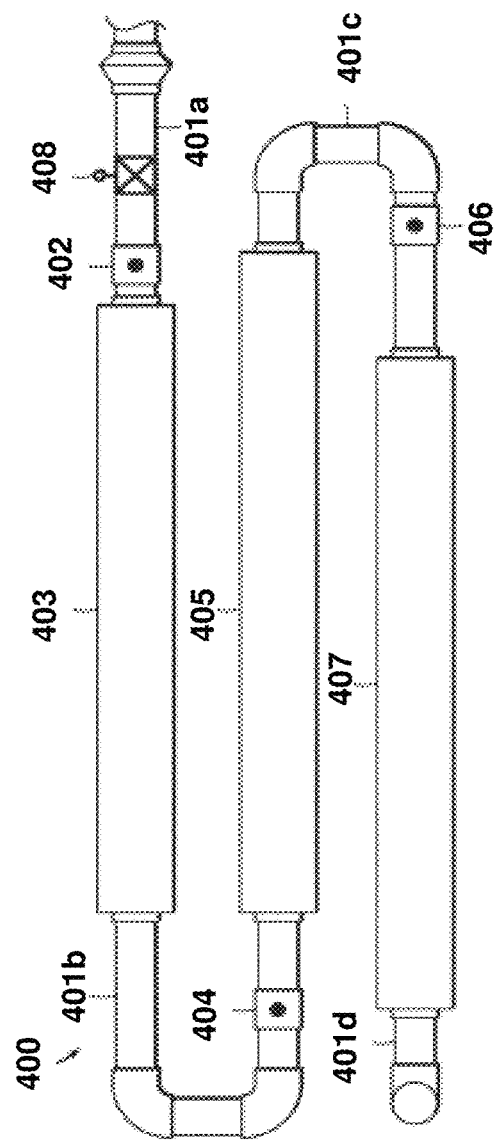
FIG. 9 is a schematic showing another exemplary system for producing hypochlorous acid according to methods of the invention.

FIG. 9 is a schematic showing another exemplary system 400 for producing hypochlorous acid according to methods of the invention. System 400 is configured for regulation of the pH of the incoming water and injecting buffer for stability. In system 400, water is introduced into pipe 401a. Pipe 401a has a pH meter 408 connected to it. pH meter 408 measures the pH of the incoming water. The pH meter 408 is connected to injection port 402. The injection port 402 allows for the introduction of at least one buffering agent to the incoming water. In the illustrated system, the buffering agent is introduced by an infusion pump that is sealably connected to port 402. Alternatively, the buffer can be included in the incoming water. In this system illustrated, the flow rate, and thus the amount, of buffering agent introduced to the water at any given time is controlled. The infusion pump can be controlled automatically or manually. The rate of introduction of the buffering agent to the water is based upon the incoming water quality (conductivity and pH level), the buffer composition, and the pressure and the flow of the incoming water. The buffer can be introduced by continuous infusion or in an intermittent manner. Since the water is flowing through the pipe 401a in a turbulent manner, there is an initial mixing of the buffering agent with the water upon introduction of the buffering to the water. This initial mixing may be sufficient to properly adjust the properties of the incoming water.

In certain embodiments, further mixing of the water and buffer is performed prior to conducting the process of producing the HOCl. In those embodiments, further mixing occurs when the water with buffering agent enters the first mixing device 403. Mixing device 403 includes all of the features discussed above with respect to mixing device 302. Mixing device 403 may be configured the same as, or differently from, mixing device 302. For example, the two mixing devices may have the same or different number of sub-chambers, the same or different diameter of apertures, the same or different sizes of sub-chambers, etc. However, like mixing device 302, mixing device 403 is configured to produce a fluidic vortex within each sub-chamber.

The solution enters mixing device 403 through an inlet in the device, which is sealably mated with pipe 401a. The solution enters the mixing chamber, and turbulent mixing occurs in each sub-chamber of the mixing device as the solution passes through members in the chamber via the apertures in each member. After mixing in the final sub-chamber, the water exits the chamber via the fluidic outlet in the mixing device, which is sealably mated to pipe 402b. The water has a pH of at least about 8.0, preferably 8.4, and a buffering capacity of pH 5.5-9.0.

The process is now conducted as described above for producing HOCl. The compound that generates the proton is next introduced to the water that is flowing through pipe 401b via injection port 404. The compound that generates the proton is introduced by an infusion pump that is sealably connected to port 404. In this manner, the flow rate, and thus the amount, of compound that generates the proton introduced to the water at any given time is controlled. The infusion pump can be controlled automatically or manually. The rate of introduction of the compound that generates the proton to the water is based upon properties of the water (conductivity and pH level), the buffer composition, and the pressure and flow rate of the water. In certain embodiments, the pump is configured to introduce from about 6.5 liters per hour to about 12 liters per hour of compound that generates the proton into the water. The compound can be introduced by continuous infusion or in an intermittent manner. Since the water is flowing though the pipes in a turbulent manner, there is an initial mixing of the compound that generates the proton with the water upon introduction of the hydrochloric acid to the water.

Further mixing occurs when the solution enters the second mixing device 405. Mixing device 405 includes all of the features discussed above with respect to mixing device 302. Mixing device 405 may be configured the same as, or differently from, mixing device 403. For example, the two mixing devices may have the same or different number of sub-chambers, the same or different diameter of apertures, the same or different sizes of sub-chambers, etc. However, like mixing device 403, mixing device 405 is configured to produce a fluidic vortex within each sub-chamber.

The solution enters mixing device 405 through an inlet in the device, which is sealably mated with pipe 401b. The solution enters the mixing chamber and turbulent mixing occurs in each sub-chamber of the mixing device as the solution pass through members in the chamber via the apertures in each member. After mixing in the final sub-chamber, the water exits the chamber via the fluidic outlet in the mixing device which is sealably mated to pipe 401c.

The compound that generates the hypochlorite anion is next introduced to the solution that is flowing through pipe 401c via injection port 406. The compound that generates the hypochlorite anion is introduced by an infusion pump that is sealably connected to port 406. In this manner, the flow rate, and thus the amount, of compound that generates the hypochlorite anion introduced to the water at any given time is controlled. The infusion pump can be controlled automatically or manually. The rate of introduction of the compound that generates the hypochlorite anion to the water is based upon properties of the solution (conductivity and pH level) and the pressure and the flow of the solution. In certain embodiments, the pump is configured to introduce about 6.5-12 liters per hour of compound that generates the hypochlorite anion into the solution. The amount introduced depends on the desired concentration of HOCl (ppm) and flow of water through the pipes. The solution can be introduced by continuous infusion or in an intermittent manner. Since the solution is flowing though the pipes in a turbulent manner, there is an initial mixing of the compound that generates the hypochlorite anion with the solution upon introduction of the compound that generates the hypochlorite anion to the solution.

Further mixing occurs when the solution enters the second mixing device 407. Mixing device 407 includes all of the features discussed above with respect to mixing device 302. Mixing device 407 may be configured the same as, or differently from, mixing devices 405 and 403. For example, the mixing devices may have the same or different number of sub-chambers, the same or different diameter of apertures, the same or different sizes of sub-chambers, etc. However, like mixing devices 405 and 403, mixing device 407 is configured to produce a fluidic vortex within each sub-chamber.

The solution enters mixing device 407 through an inlet in the device, which is sealably mated with pipe 401c. The solution enters the mixing chamber, and turbulent mixing occurs in each sub-chamber of the mixing device as the solution passes through members in the chamber via the apertures in each member. After mixing in the final sub-chamber, the water exits the chamber via the fluidic outlet in the mixing device, which is sealably mated to pipe 401d.

At this point, the reaction has been completed and the HOCl has been formed. The produced HOCl can be measured and collected as described above. Pipe 401d can be connected to a switch valve that switches between a waste line and a product collection line. The valve includes a pH meter and a conductivity measuring device. These devices measure the concentration, purity, and pH of the HOCl being produced and provide feedback for altering such properties of the produced HOCl. Once the HOCl being produced in pipe 401d meets the required concentration, purity, and pH, the valve switches from the waste line to the product collection line to collect the desired product.

Figure 10:
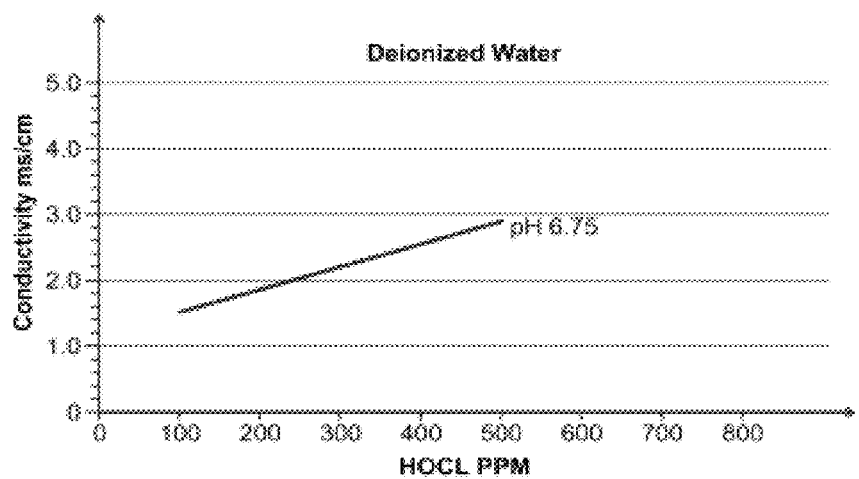
FIG. 10 is a graph of a calibration curve showing HOCl concentration (ppm) calculated indirectly versus conductivity.

FIG. 10 shows a curve of the conductivity at different known concentrations of HOCl and OCl⁻ in the same matrix. The calibration curve is used in combination with the pH meter to regulate the titrations and control the process.

In another embodiment, a deionizer is placed in-line with incoming water. The deionizer deionizes the water, and then a buffering agent is added to the deionized water. The production process is then conducted as described for embodiments of system 200 to produce water having a pH of at least about 8, for example 8.4, and a buffering capacity of pH 6-8.

The HOCl produced by the above process can be used in numerous different applications, for example, in the medical, foodservice, food retail, agricultural, wound care, laboratory, hospitality, dental, delignification, or floral industries.

Any and all references and citations to other documents, such as patents, patent applications, patent publications, journals, books, papers, web contents, that have been made throughout this disclosure are hereby incorporated herein by reference in their entirety for all purposes.

The invention may be embodied in other specific forms without departing from the spirit or essential characteristics thereof. The foregoing embodiments are therefore to be considered in all respects illustrative rather than limiting on the invention described herein.

Compositions of Acetic Acid and Hypochlorous Acid for Biofilm Treatment

The disclosed formulations of acetic acid and hypochlorous acid are superior for treating biofilms on surfaces including skin or other tissue. The compositions use a balanced formula where the combination of acetic acid and hypochlorous acid provide greater disinfecting qualities than either substance alone. In fact the present invention recognizes that the particular disclosed combinations provide greater disinfecting power than would be expected by adding the acetic acid and hypochlorous acid. In other words, the compositions have been found to be greater than the sum of their parts. These benefits are shown in the accompanying data in FIGS. 15-24, which demonstrate how the balanced compositions of acetic acid and hypochlorous acid provide enhanced disinfecting capabilities against biofilms and outperform all other products on the market. The differences in performance are shown across a wide range of concentrations. Additionally, since acetic acid is toxic at high concentrations, the prior art has taught away from its use on skin or other tissue, except in trace amounts. Some of the disclosed compositions contain acetic acid at 2% or greater, and when in combination with HOCl have proven to be safe and effective for treating skin and other tissues. The HOCl in these compositions has been found to have a modulating effect of the acetic acid. This allows the compositions to take advantage of the antimicrobial properties of acetic acid without causing harm to the tissue. Additionally, HOCl has an analgesic function, so it also allows higher concentrations of HAc to be used on skin or other tissue without causing excessive pain or discomfort to the patient.

Figure 15:
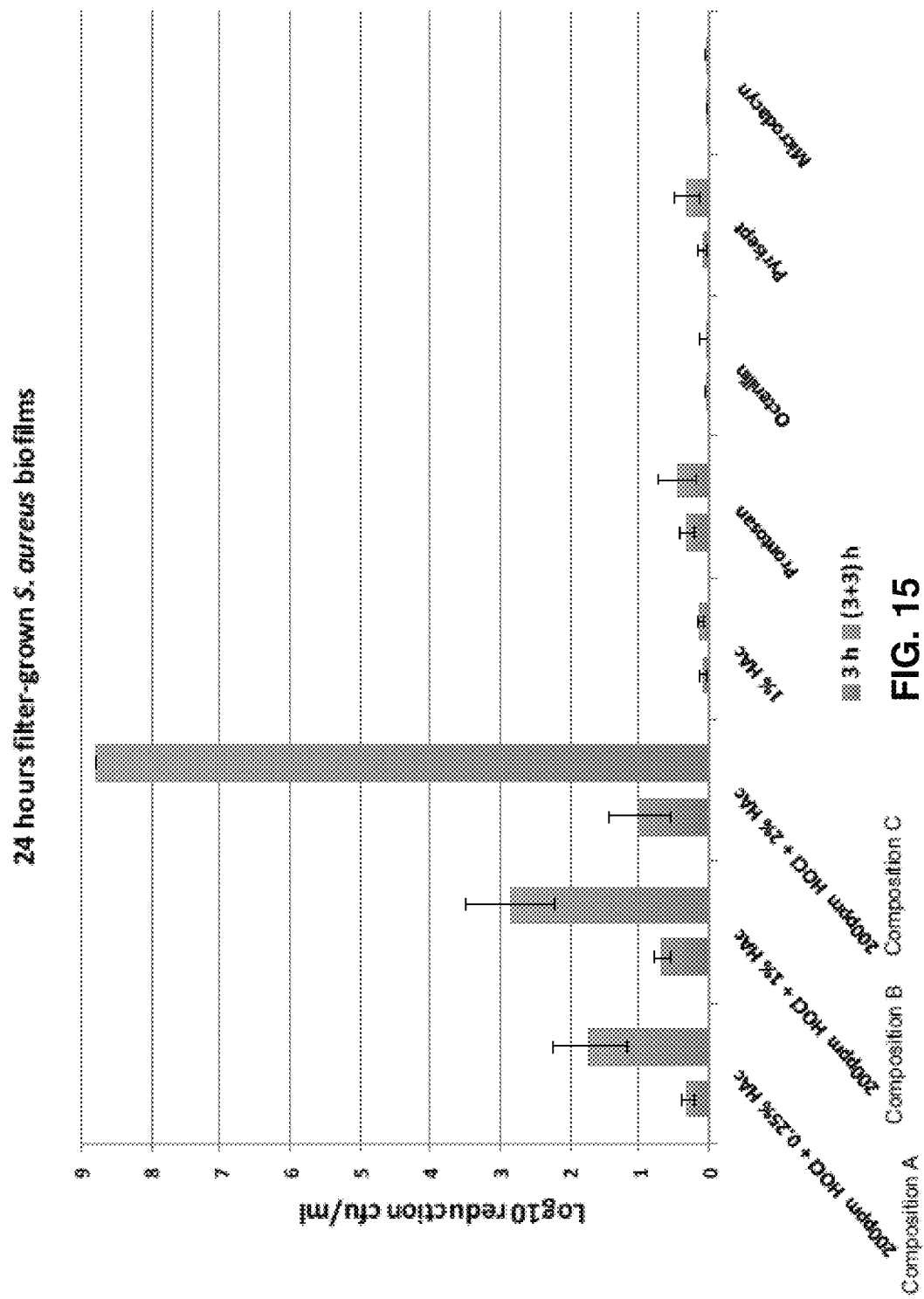

FIG. 15 for example, shows a comparison of various concentrations of HOCl and acetic acid against other commercially available antimicrobial compositions. Eight different treatments were tested, as listed along the x-axis. Each composition was exposed to a 24-hour filter-grown S. aureus biofilm, and the reduction in biofilm was measured in colony-forming units per milliliter (cfu/ml) and reported on a log scale along the y-axis. Measurements of the reduction in biofilm were recorded at 3 hours and 6 hours. Each column therefore has two bars, and shows the effect of each composition on the biofilm over time.

The first three columns show the results of 200 ppm HOCl with three different concentrations of acetic acid (0.25%, 1.0%, and 2.0%, respectively). The fourth column shows 1% acetic acid alone. The next four columns show commercially available antimicrobial products: Prontosan; Octenilin; Pyrisept; and Microdacyn, which is a hypochlorous acid composition.

The results show that all three combinations of acetic acid and hypochlorous acid were more effective against the biofilm than any of the other compositions. At 3 hours, test composition A (200 ppm HOCl and 0.25% HAc) performed approximately as well as the Prontosan, the current market leader in biofilm treatment. It also far outperformed the 1%

HAc or the other commercially available products. After 6 hours, however, composition A showed much greater efficacy than even Protosan.

Meanwhile, test composition B (200 ppm HOCl and 1.0% HAc) was even more effective at treating biofilm. Comparing composition B with the 1% HAc (in the fourth column) shows the unexpected benefit of the addition of HOCl. Despite having the same concentration of acetic acid, composition B far outperforms the 1% HAc alone at both 3 hours and 6 hours. Composition C (200 ppm HOCl and 2.0% HAc) showed by far the greatest reduction in biofilm among the tested compositions. At both 3 and 6 hours, it was several orders of magnitude more effective than the commercially available products.

These data show that in addition to being more effective in reducing biofilm than any of the commercially available products, the compositions containing both acetic acid and hypochlorous acid were more effective than acetic acid alone (1% HAc) or hypochlorous acid alone (microdacyn), and those superior results cannot be explained merely by the additive effect of the two components. Without being bound by any particular mechanism, the data show that the acetic acid and hypochlorous acid combination provides a synergistic effect that allows the composition to be more effective than would otherwise be predicted based on the efficacy of each component alone.

Figure 16:
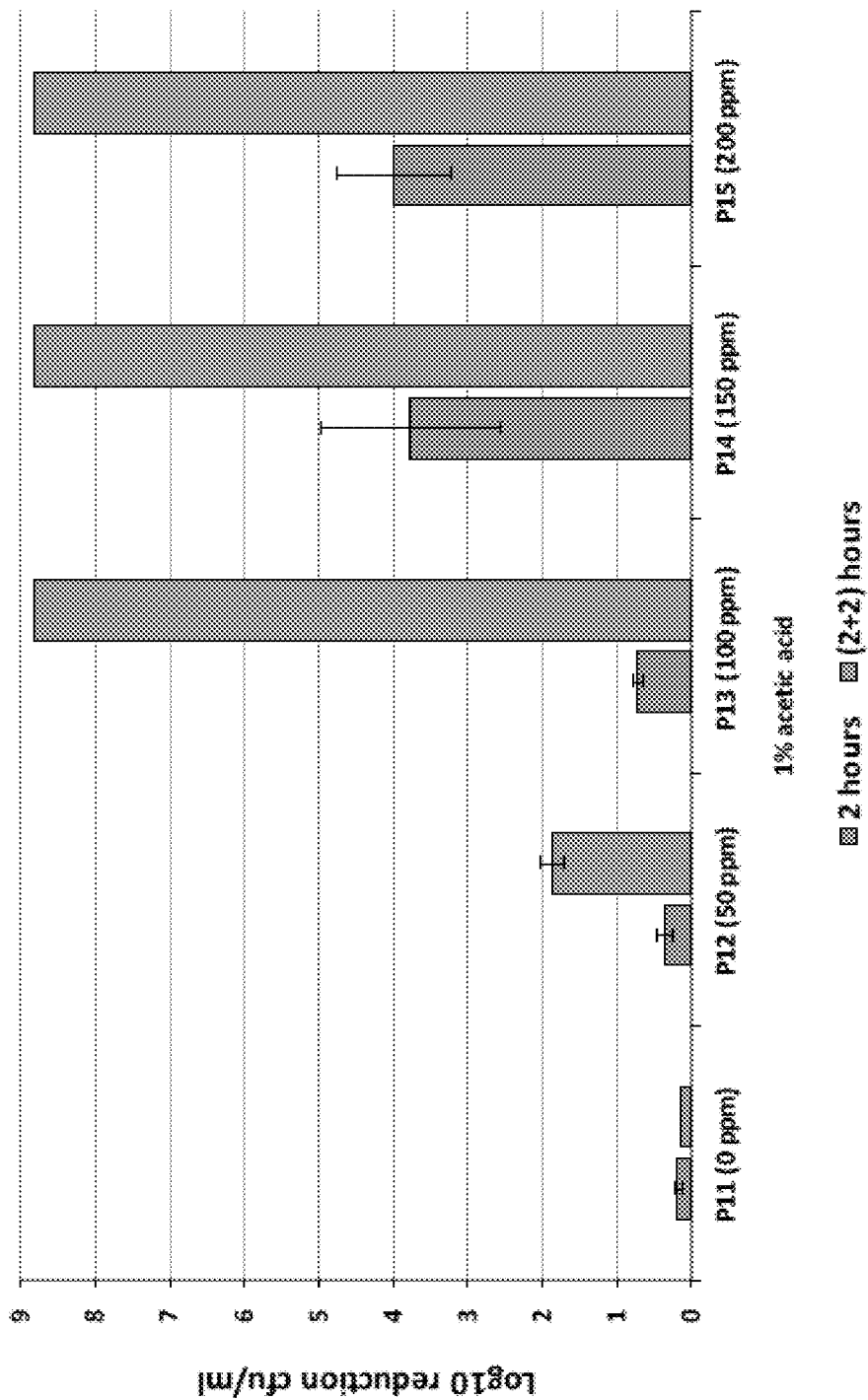

FIGS. 16-19 show the effects of various compositions of HOCl and HAc on P. aeruginosa biofilms. FIG. 16 shows a comparison of compositions having 1% acetic acid and varying concentrations of HOCl. Five different treatments were tested with HOCl in concentrations of 0 ppm, 50 ppm, 100 ppm, 150 ppm, and 200 ppm. Each composition was exposed to a 24-hour filter-grown P. aeruginosa biofilm, and the reduction in biofilm was measured in colony-forming units per milliliter (cfu/ml) and reported on a log scale along the y-axis. Measurements of the reduction in biofilm were recorded at 2 hours and 4 hours. As shown in the graph, the reduction at 2 hours was greater with higher concentrations of HOCl, with a particularly significant spike at 150 ppm. At 4 hours, the spike occurs at even lower concentrations of HOCl.

Figure 17:
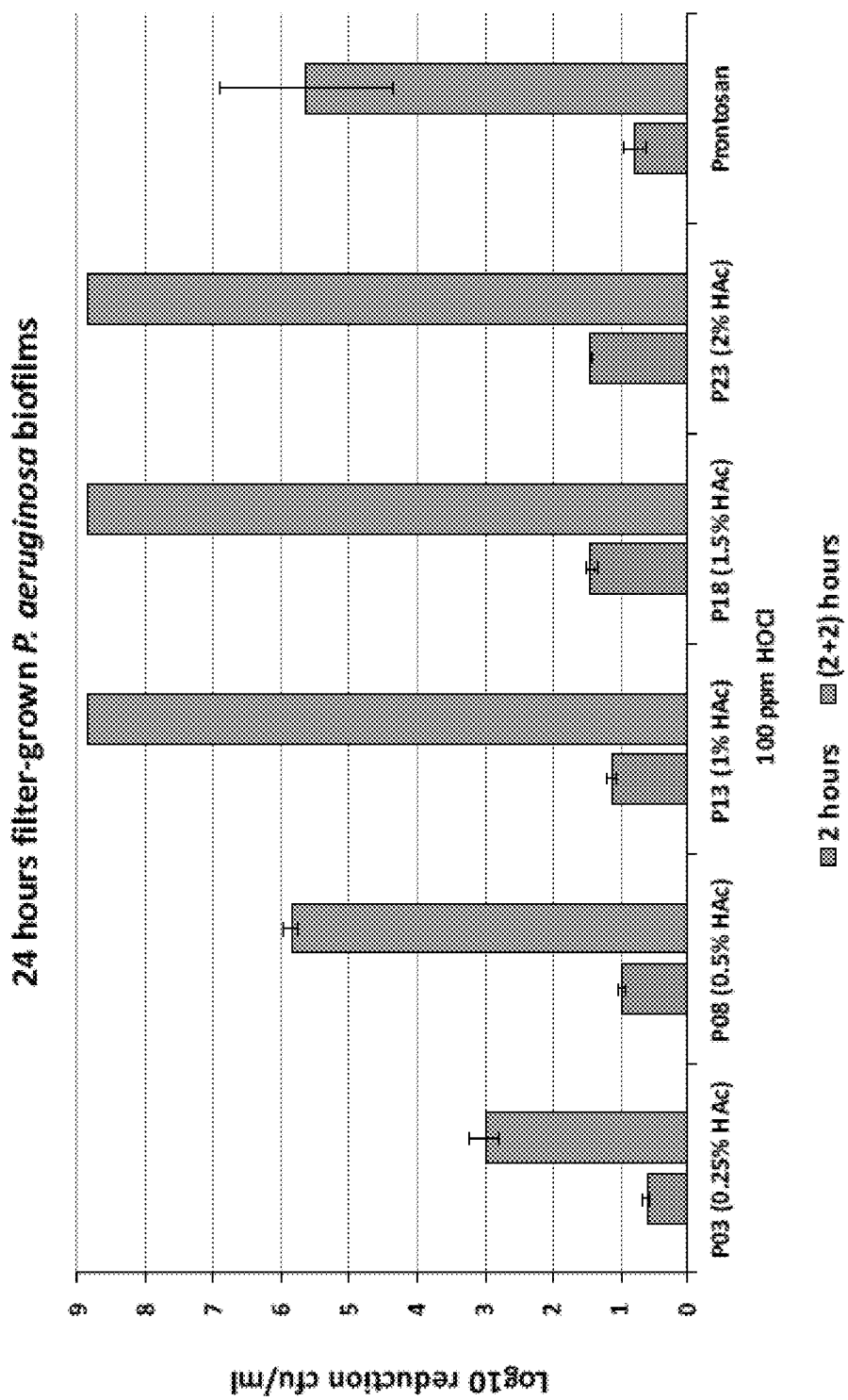
Figure 18:
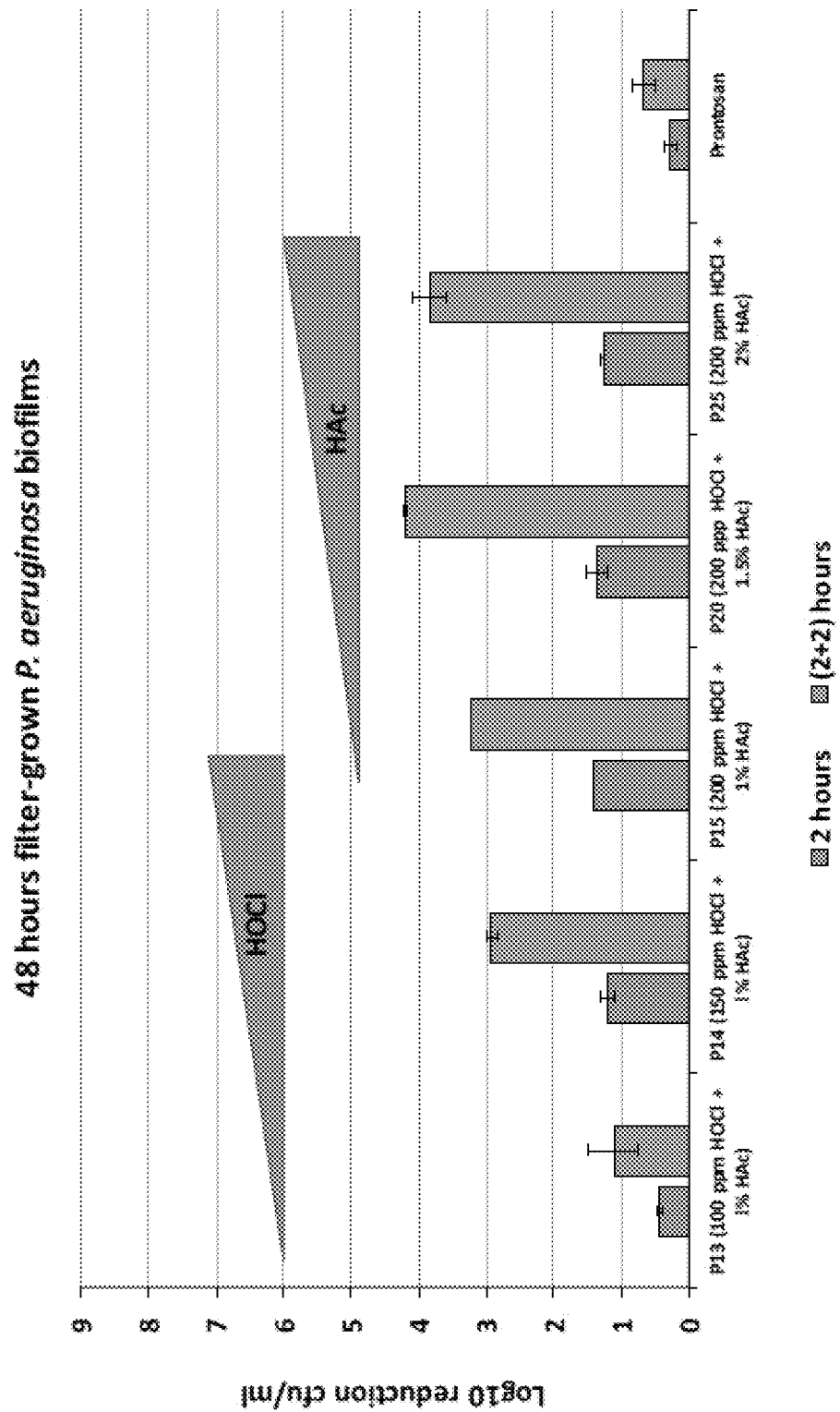

FIG. 17 shows the effects on P. aeruginosa of different compositions where the concentration of HOCl is maintained at 100 ppm and the percentage of acetic acid varies from 0.25% to 2%. FIG. 18 shows the effects as both HOCl and HAc increase.

FIGS. 19-24 show different compositions of HOCl and HAc against S. aureus and P. aeruginosa under various conditions. The figures show the superior results obtained with combinations of hypochlorous acid and acetic acid, which demonstrate the synergistic effect of those two compounds.

The various disclosed formulations may be effective for treating biofilm infections in different types of tissue. For example, the 200 ppm HOCl and 0.25% HAc composition is useful for topical applications such as hand disinfection or mouth wash. This composition is more effective than other commercially available products at treating surface-level biofilms as shown in FIG. 15. For treating penetrating deeper into tissue, or for clearing particularly bad biofilm infections or invasive biofilms that have penetrated beneath the surface, a higher percentage of HAc may be used, such as the formulation of 200 ppm HOCl with 2% HAc. This composition is useful for treating infected wounds, preventing biofilm in wounds, treating eczema, or treating other infections. This formulation has been found to be effective for combatting biofilms that have formed in the root of teeth.

Figure 20:
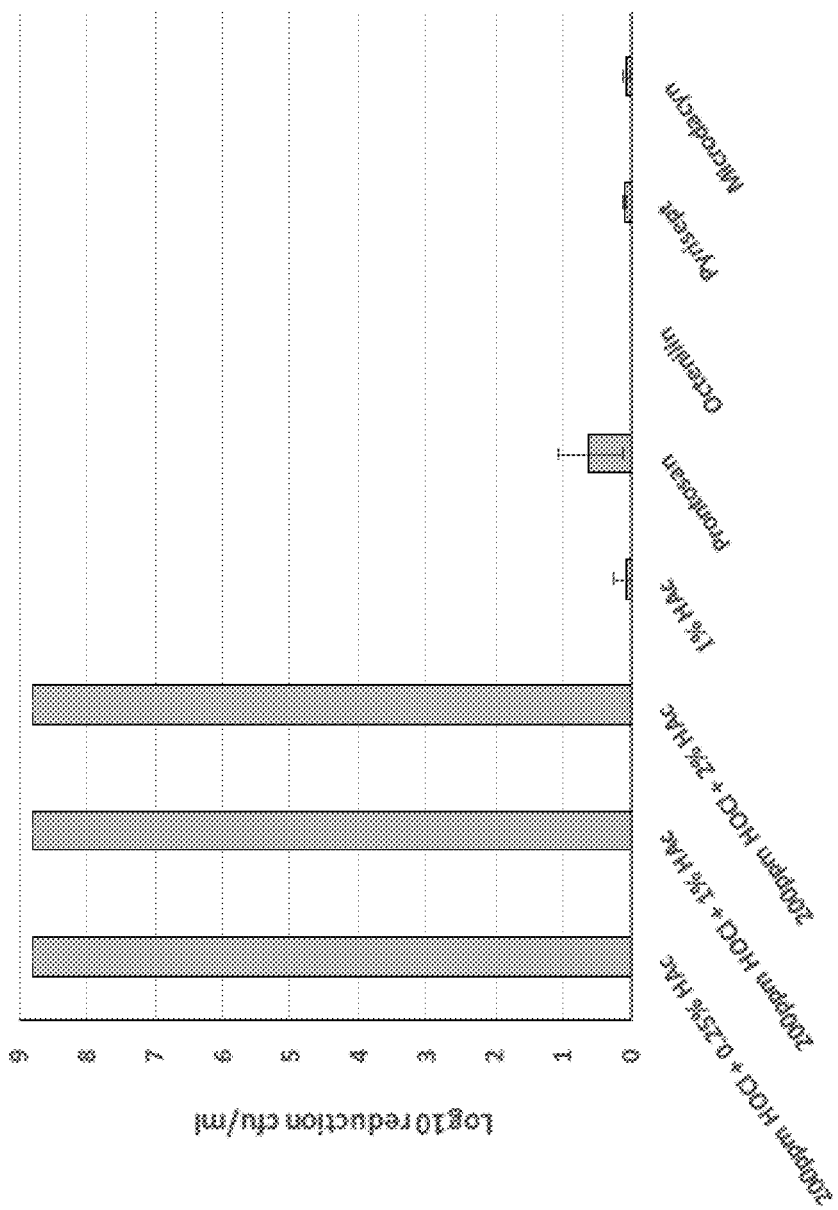
Figure 21:
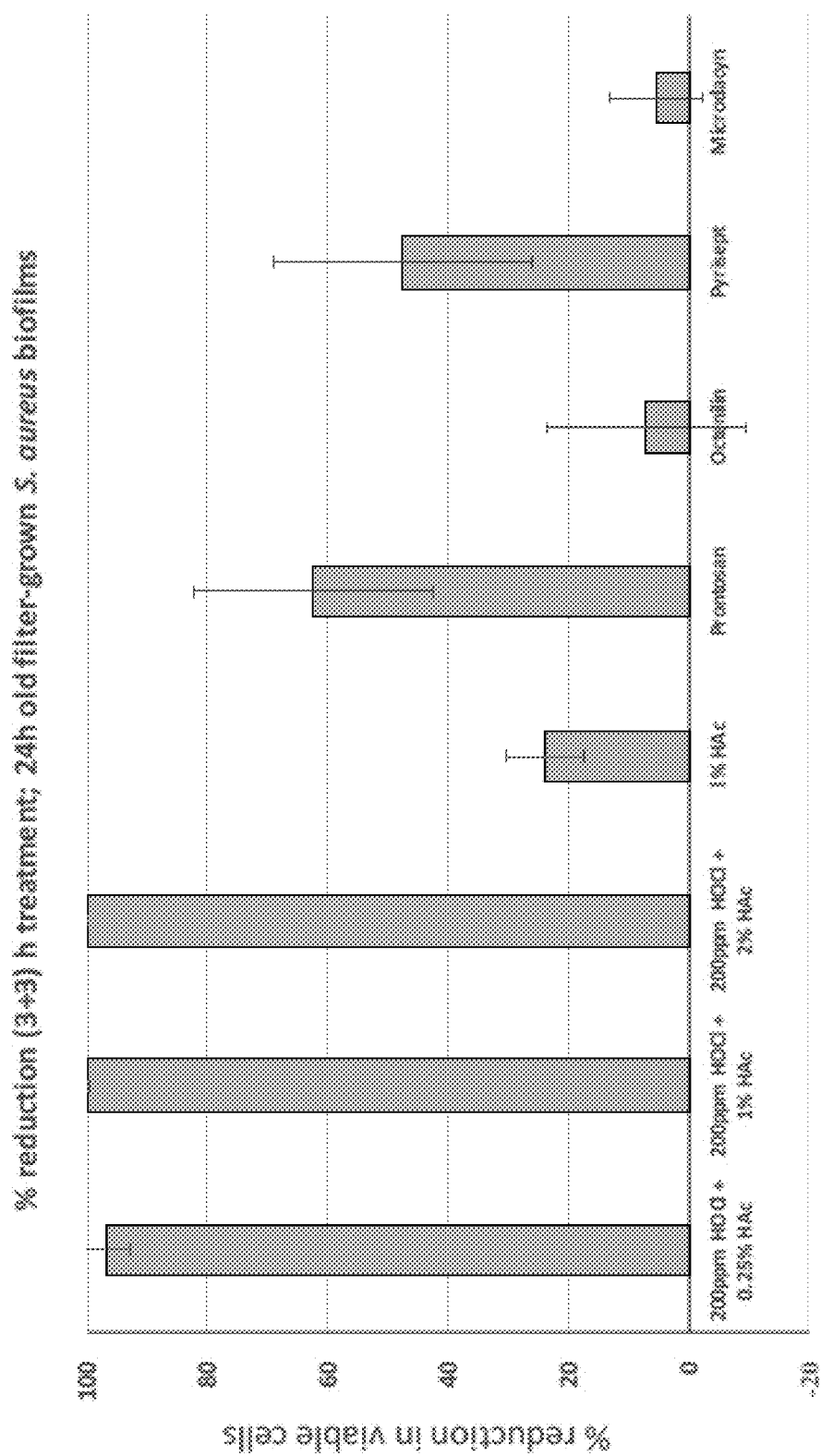

FIGS. 20-21 show additional data supporting the unexpected efficacy of acetic acid and hypochlorous acid compositions on various biofilms, particularly as compared to prior art and commercially available compositions. As the figures make clear, various compositions that balance in the concentrations of HOCl and HAc in different ways provide an assortment of disinfecting compositions that can target different types of biofilms on different types of tissue. Another benefit of the disclosed HOCl and HAc compositions is that while they are particularly effective at reducing pathogenic biofilms, they have been found not to inhibit growth of "good" biofilms and other microbes that live symbiotically on and in tissue. In some trials, the good biofilm was reduced to a lesser expen than the pathogenic biofilm, and it grew back faster than the target biofilm did. Especially compared with alcohol-based disinfectants, the disclosed compositions were more effective at targeting the pathogenic biofilm infection without damaging the good microbes. The disclosed compositions therefore are a targeted treatment, combating biofilm infections without causing harm to the body's natural flora.

EXAMPLES

Example 1

Product Analysis

When spectrophotometry is expanded to cover the visible range it is possible to detect colors. The gases generally produced during production of HOCl are $ClO_2$, $Cl_2O$ and $Cl_2$, all of which are detectable in the visible range as yellow or yellow-red. Tzanavaras et al. (*Central European J. of Chemistry*, 2007, 5(1)1-12).

Figure 11:
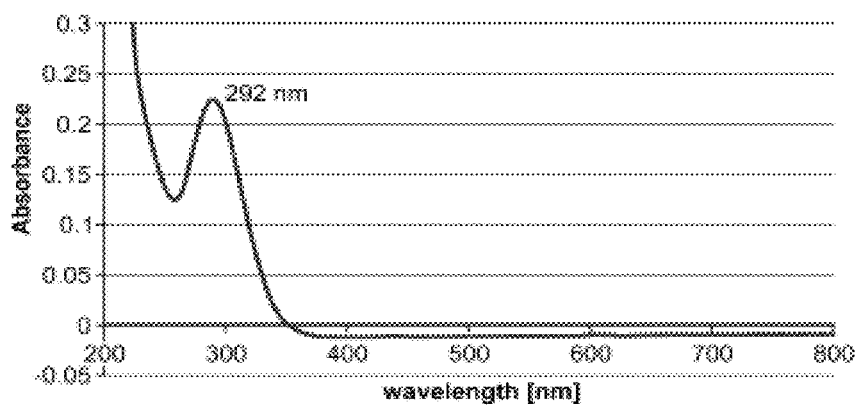
FIG. 11 is a graph showing a spectrophotometric analysis of HOCl produced by a method of the invention.

FIG. 11 is a graph of absorbance data for a sample produced by the methods described. The data shows that the HOCl produced by methods on the invention shows no absorption from colored gases as shown by the lack of colored substance. It is known that HOCl produces a peak at 292 nm (Feng et al. 2007, *J. Environ. Eng. Sci.* 6, 277-284).

Example 2

Product Analysis

HOCl produced by the process described above was stored under heat stress at 40° C. in order to accelerate degradation using four different types of aqueous solutions: (1) reagent grade water (deionized water); (2) tap water; (3) reagent grade water with a phosphate buffer; and (4) tap water with a phosphate buffer. Characteristics of the HOCl product were monitored after the initial reaction (T=0); four weeks (T=4); eight weeks (T=8); and twelve weeks (T=12).

Figure 12:
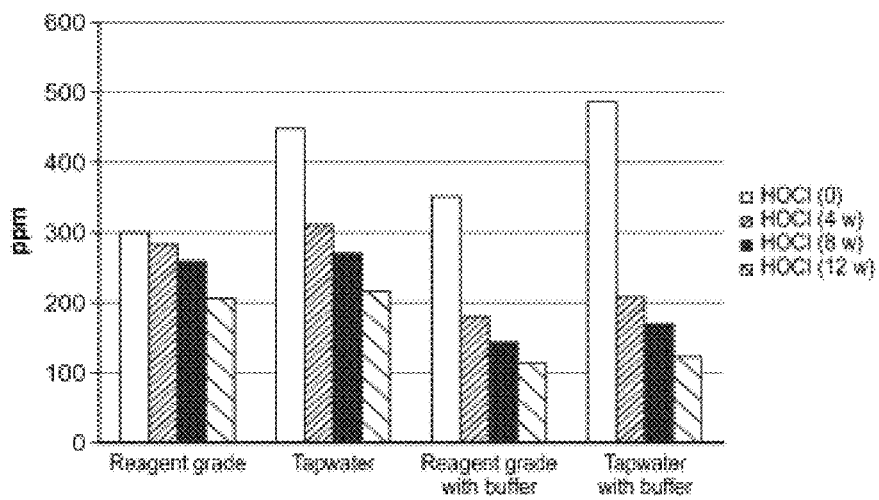
FIG. 12 is a graph showing the amount (parts per million (ppm)) of HOCl initially produced (T=0) and its stability over time.

FIG. 12 is a graph showing the amount (parts per million (ppm)) of HOCl initially produced (T=0) and its stability over time. The data show that the reagent grade water (deionized water) without phosphate buffer is the most stable over the twelve weeks, showing the least amount of product degradation from the initial amount produced. The deionized water produces a much more stable product than that produced using tap water. Additionally, and surprisingly, the data show that phosphate buffer may negatively impact amount of HOCl product produced.

Figure 13:
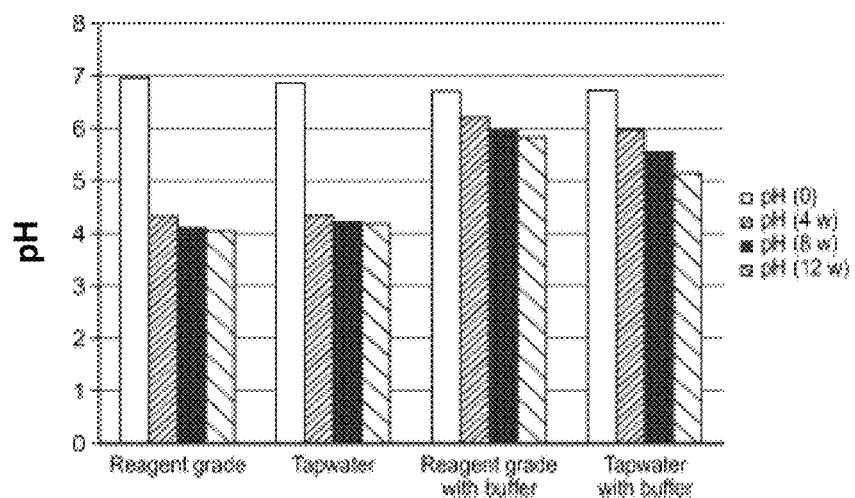
FIG. 13 is a graph showing how the pH of the HOCl product changed over time.

FIG. 13 is a graph showing how the pH of the HOCl product changed over time. In all cases, the pH decreased over time. However, for all cases, the pH stayed in the range of pH 4-7 over the twelve weeks.

Figure 14:
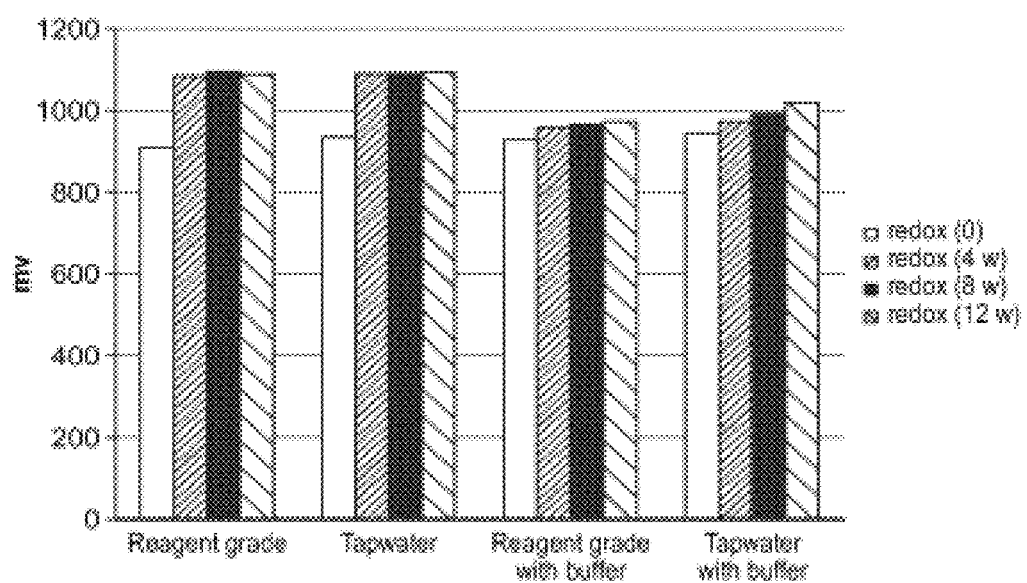
FIG. 14 is a graph showing the oxidation and reduction (redox) of the HOCl product over time.

FIG. 14 is a graph showing the oxidation capacity of the HOCl product over time. The data show that the product retained oxidation capacity over the twelve weeks regardless of the starting water.

Example 3

Acetic Acid Compared to Hydrochloric Acid

Using the above described process, HOCl was produced using hydrochloric acid (HCl) or acetic acid and thereafter stored under heat stress at 40° C. The amount of HOCl initially produced was recorded (T=0) and then the amount of HOCl product remaining after twelve days was recorded. Three batches of each were produced. The data for the HCl produced HOCl is shown in Table 1. The data for the acetic acid produced HOCl is shown in Table 2.

TABLE 1

HOCl produced with HCl

| Batch number | Initial amount (ppm) | Initial pH | Amount after 12 days (ppm) | pH after 12 days | Amount of degradation | Amount of pH change |
|---|---|---|---|---|---|---|
| 1 | 192 | 7.12 | 159 | 5.71 | 17.2% | 19.8% |
| 2 | 183 | 5.88 | 147 | 4.01 | 19.7% | 31.8% |
| 3 | 189 | 5.21 | 154 | 3.97 | 18.5% | 23.8% |

TABLE 2

HOCl produced with acetic acid

| Batch number | Initial amount (ppm) | Initial pH | Amount after 12 days (ppm) | pH after 12 days | Amount of degradation | Amount of pH change |
|---|---|---|---|---|---|---|
| 1 | 205 | 4.62 | 180 | 4.50 | 124% | 27% |
| 2 | 205 | 5.33 | 178 | 5.04 | 133% | 54% |
| 3 | 207 | 4.07 | 178 | 3.89 | 139% | 46% |

The data show that using acetic acid provides greater product stability, most likely due to greater stability in the pH. Without being limited by any particular theory or mechanism of action, it is believed that the different protonation capacity of acetic acid as compared to hydrochloric acid, i.e., acetic acid donates fewer protons to a liquid than hydrochloric acid, results in greater HOCl stability over time.

What is claimed is:

1. An anti-microbial composition comprising:
    an aqueous solution of hypochlorous acid and a zinc metal ion, the solution being substantially free of air and being encapsulated in a nanoparticle.

2. The composition of claim 1, wherein the composition is substantially free of chlorine gas.

3. The composition of claim 1, wherein the hypochlorous acid is in an aqueous solution having a pH from about 4.5 to about 7.5.

4. The composition of claim 3, wherein the aqueous solution comprises a buffering agent.

5. The composition of claim 4, wherein the buffering agent is acetic acid.

6. The composition of claim 1, wherein the nanoparticle comprises a polymer.

7. The composition of claim 1, wherein the nanoparticle comprises a liposome.

8. The composition of claim 1, wherein the nanoparticle comprises a hydrogel.

* * * * *